(12) United States Patent
Kahlman

(10) Patent No.: US 7,250,759 B2
(45) Date of Patent: Jul. 31, 2007

(54) INTEGRATED 1/F NOISE REMOVAL METHOD FOR A MAGNETO-RESISTIVE NANO-PARTICLE SENSOR

(75) Inventor: Josephus Arnoldus Henricus Maria Kahlman, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 20 days.

(21) Appl. No.: 10/566,664

(22) PCT Filed: Jul. 16, 2004

(86) PCT No.: PCT/IB2004/051243
§ 371 (c)(1), (2), (4) Date: Jan. 27, 2006

(87) PCT Pub. No.: WO2005/010503
PCT Pub. Date: Feb. 3, 2005

(65) Prior Publication Data
US 2006/0214658 A1    Sep. 28, 2006

(30) Foreign Application Priority Data

| Jul. 30, 2003 | (EP) | 03102353 |
| Jul. 30, 2003 | (EP) | 03102356 |
| Dec. 11, 2003 | (EP) | 03104632 |

(51) Int. Cl.
*G01R 33/09* (2006.01)
*G01N 33/50* (2006.01)

(52) U.S. Cl. .................. 324/252; 324/249; 436/806
(58) Field of Classification Search ............. 324/249, 324/252; 257/421–422; 436/806
See application file for complete search history.

(56) References Cited

U.S. PATENT DOCUMENTS

| 5,825,595 | A | | 10/1998 | Gill | |
| 5,922,537 | A | * | 7/1999 | Ewart et al. | 435/6 |
| 5,981,297 | A | * | 11/1999 | Baselt | 436/514 |

* cited by examiner

*Primary Examiner*—Bot LeDynh

(57) ABSTRACT

The present invention provides an integrated circuit and a method for noise removal in a magnetic nano-particle sensor device. The method of the present invention comprises the steps of sending a conductor current through a conductor to generate a first horizontal magnetic field component at the location of a magneto-resistive sensor. In a further step the optimal operation point of the magneto-resistive sensor is determined by minimizing the noise at the output of the magneto-resistive sensor by means of a noise optimization circuit. By applying an external magnetic field such that nano-particles in the vicinity of the sensor are vertically magnetized, a second horizontal magnetic field component is generated at the location of the sensor. Then, the conductor current is adjusted such that the first horizontal magnetic field component compensates for the second horizontal magnetic field component. The magnitude of the conductor current necessary for this compensation is a measure for the amount of nano-particles present at the sensor.

21 Claims, 7 Drawing Sheets

INTEGRATED 1/F NOISE REMOVAL METHOD FOR A MAGNETO-RESISTIVE NANO-PARTICLE SENSOR

The present invention relates to sensor devices for the detection of magnetic nano-particles and more particularly to an integrated circuit and a method for noise removal in a magneto-resistive nano-particle sensor.

Magneto-resistive sensors based on AMR (anisotropic magneto resistance), GMR (giant magneto resistance) and TMR (tunnel magneto resistance) elements are nowadays gaining importance. Besides the known high speed applications such as magnetic hard disk heads and MRAM, new relatively low bandwidth applications appear in the field of molecular diagnostics (MDx), current sensing in IC's, automotive, etc.

AMR occurs in ferro- and ferrimagnetic materials. It is a change in resistance when a magnetic field is applied which is not parallel to the current flow in a thin strip of ferrous material. The resistance is maximum when the magnetic field applied is perpendicular to the current flow. AMR elements are characterised by high sensitivity, wide operating temperature range, low and stable offset and the wide frequency range, up to units of MHz. Using the proper technological process enables to obtain the linear dependence of the change of resistance on the magnetic field intensity in one specific direction.

In GMR technology, structures have been developed in which a first and a second very thin magnetic film are brought very close together. The first magnetic film is pinned, which means that its magnetic orientation is fixed, usually by holding it in close proximity to an exchange layer, a layer of anti-ferromagnetic material that fixes the first magnetic film's magnetic orientation. The second magnetic film, or sensor film, has a free, variable magnetic orientation. Changes in the magnetic field, in the present case originating from changes in the magnetisation of magnetic material, such as superparamagnetic particles, cause a rotation of the sensor film's magnetic orientation, which in turn, increases or decreases resistance of the entire sensor structure. Low resistance occurs when the sensor and pinned films are magnetically oriented in the same direction. Higher resistance occurs when the magnetic orientations of the sensor and pinned films oppose each other.

TMR can be observed in systems made of two ferromagnetic layers separated by an isolating (tunnel) barrier. This barrier must be very thin, i.e., of the order of 1 nm. Only then, electrons can tunnel through this barrier, which is again an entirely quantum-mechanical transport process. The magnetic alignment of one layer can be changed without affecting the other. Changes in the magnetic field, in the present case again originating from changes in the magnetisation of magnetic material, such as superparamagnetic particles, cause a rotation of the sensor film's magnetic orientation, which in turn, increases or decreases resistance of the entire sensor structure.

In patent application WO 03/054523 entitled "Sensor and method for measuring the areal density of magnetic nano-particles on a micro-array", a magnetic nano-particle biosensor for the detection of biological molecules on a micro-array or biochip, which sensor uses GMR sensor elements, is disclosed. A magneto-resistive sensor 1, as described in one embodiment of the cited document, is illustrated in FIG. 1. The sensor 1 comprises a first GMR sensor element 2 and a second GMR sensor element 3 integrated in a biochip substrate 4 at a distance d under the surface 5 of the substrate 4. The surface 5 of the biochip substrate 4 has to be modified in order to allow nano-particles 6 to bind to it.

In FIG. 1 a co-ordinate system has been introduced and according to that co-ordinate system, the GMR elements 2, 3 that have a length w, extend in the y direction over a certain length. If the magneto-resistive sensor elements 2, 3 lie in the xy plane, the GMR sensor elements 2, 3 detect the x-component of the magnetic field, i.e. they have a sensitive direction in the x-direction. In order to read out the biochip, the superparamagnetic nano-particles 6 bound to it are magnetized by an external, uniform magnetic field perpendicular to the plane of the biochip. The perpendicular magnetic field orientates the higher magnetic field at the ends of the magnetic dipoles formed by the nano-particles 6 towards and close to the first and second GMR sensor elements 2, 3. The magnetized nano-particles 6 produce regions of opposite magnetic induction vectors in the plane of the underlying GMR films and the resulting magnetic field is detected by the first and second GMR sensor elements 2, 3. The outputs of the GMR sensor elements 2, 3 are fed to a comparator.

In the described document, measurements are carried out in the saturation region of the magnetic nano-particles 6. In order to fully saturate the nano-particles or nano-beads (typically 0.025 $Am^2/g$ or more for 50 nm beads) at least an 80 kA/m (=0.1 Tesla) external magnetic field is typically required. In order to remove common mode disturbances and 1/f noise this field is preferably alternated. Careful mechanical alignment is required in order to avoid sensor saturation due to in-plane field components, which typically occurs at +/−5 mT, 4 kA/m. Due to practical issues the maximum field strength is typically limited to 40 kA/m and 10 Hz alternating frequency, dissipating 8 Watt (1 A at 8 V) in the coil.

A disadvantage of the method and device of the prior art is that the achievable signal-to-noise ratio (SNR) of GMR and TMR elements in the low frequency regime (typically 0-20 kHz) is limited by the presence of (magnetic) 1/f noise in these elements itself, by the electronic noise properties of the amplifiers, such as e.g. noise, offset, drift, and by unwanted magnetic fields. The 1/f noise power density is proportional to the inverse of the frequency, and often dominates below 100 Hz in electronic components. In magneto-resistive sensors, it is known that above a certain corner frequency $f_c \approx 50$ kHz the thermal white noise becomes dominant. The white-noise level limits the theoretically achievable detection limit. If the SNR is smaller than 1, it is difficult to get a meaningful measurement. There are several methods of improving the SNR. A known method for removing the low frequency noise is to apply a chopping method where the external magnetic field for magnetising the nano-particles is reversed at a rate above $f_c$. However, this method requires high power consumption, an external coil and yoke and extra connections and is therefore not suitable if small form factor biosensors are needed.

It is an object of the present invention to provide a method and device for noise removal in a magneto-resistive sensor that may be used in a nano-particle sensor device.

The above objective is accomplished by a method and device according to the present invention.

The present invention provides an integrated circuit for noise removal in magnetic nano-particle sensor device. The integrated circuit comprises at least one first magnetic field generator and at least one magneto-resistive sensor. According to one embodiment of the invention, the at least one first magnetic field generator may comprise a conductor. The at least one first magnetic field generator is suitable for generating a first magnetic field component in a sensitive direction of the at least one magneto-resistive sensor. The integrated circuit furthermore comprises a means for determining an operation point of the at least one magneto-resistive sensor. An optimal operation point needs to be determined for which the signal-to-noise ratio is maximised, i.e. the largest SNR on the detection characteristic of the sensor has to be found. For the present invention, the signal-to-noise ratio (SNR) may be at least 1. The absolute value of the SNR depends on the amplitude of the applied external magnetic field and on the sensor noise power. Furthermore, there is a second magnetic field generator for generating a magnetic field for magnetising the nano-particles to thereby generate a second magnetic field component in the sensitive direction of the at least one magneto-resistive sensor. The second magnetic field generator may be a magnetic field generator external to the integrated circuit. In another embodiment, the second magnetic field generator may be part of the integrated circuit. In one embodiment of the invention the second magnetic field generator may be a permanent magnet. In another embodiment, the second magnetic field generator may comprise one or more conductors. Furthermore, the integrated circuit comprises at least one noise optimisation circuit adapted for stabilising the net magnetic field strength in the sensor by compensating for the second magnetic field component.

The second magnetic field generator may be positioned in a direction perpendicular to the device or at an angle with respect to a perpendicular to the sensor device. However, the latter can easily saturate the sensor because the external magnetic field is much larger than the dynamic range of the sensor. Within its dynamic range, the invention can prevent saturation of the sensor.

In an embodiment of the present invention the at least one magneto-resistive sensor may comprise an upper side and a lower side, the upper side and lower side being opposite to each other. In this embodiment, the at least one magnetic field generator may be positioned at the lower side of the at least one magneto-resistive sensor.

In another embodiment, the integrated circuit may comprise two magneto-resistive sensors adjacent to each other and a magnetic field generator positioned at the lower side of each magneto-resistive sensor.

In the present invention, the magneto-resistive sensor may be a GMR, a TMR or an AMR sensor and may have a long and narrow stripe geometry. Furthermore, in another embodiment the first magnetic field generator may be integrated into the magnetoresistive sensor.

In one embodiment the noise optimisation circuit may comprise an integrator device. In another embodiment of the invention, the noise optimisation circuit may furthermore comprise a harmonic modulation source.

Furthermore, the present invention provides a biochip comprising the integrated circuit according to the invention.

The invention furthermore provides a method for noise removal in a magnetic nano-particle sensor device. The method comprises:
  generating a first magnetic field component in a sensitive direction of a magneto-resistive sensor,
  determining an operation point of the magneto-resistive sensor by minimizing the noise at the output of the magneto-resistive sensor,
  applying a second magnetic field for magnetising nano-particles thus generating a second magnetic field component in the sensitive direction of the magneto-resistive sensor.

The signal to noise ration for the operation point may be as high as possible and may be at least 1.

The second magnetic field may be generated by a permanent magnet or by one or more additional conductors. The second magnetic field generator may be positioned in a direction substantially perpendicular to the sensor device or at an angle with respect to a perpendicular to the sensor device.

In one embodiment of the invention, the first magnetic field component may be generated by flowing a conductor current through a conductor. Adjusting the first magnetic field component may be performed by adjusting the conductor current through the conductor.

In another embodiment, the method of the present invention may furthermore comprise:
  determining an operation point of a second magneto-resistive sensor by minimizing the noise at the output of the second magneto-resistive sensor and
  calibrating the difference between the output of the first magneto-resistive sensor and the second magneto-resistive sensor to zero.

Determining an operation point of the second magneto-resistive sensor may be performed by determining an optimal operation point for which the signal to noise ratio may be as high as possible and may be at least 1.

Furthermore, the method of the present invention may be applied during the manufacturing of an integrated circuit.

The present invention furthermore provides the use of the integrated circuit according to the invention for molecular diagnostics, biological sample analysis or chemical sample analysis.

An advantage of the method of the present invention is that the generic noise generated in a magneto-resistive sensor may be reduced by stabilising the sensor operation point. A further advantage is that the method compensates for perpendicular alignment errors that cause in-plane magnetic fields which may drive the magneto-resistive sensor in its noise-sensitive area or in saturation. Another advantage of the present invention is that the method of the present invention may give rise to small form factor, low cost sensor devices.

These and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

Figure 1:
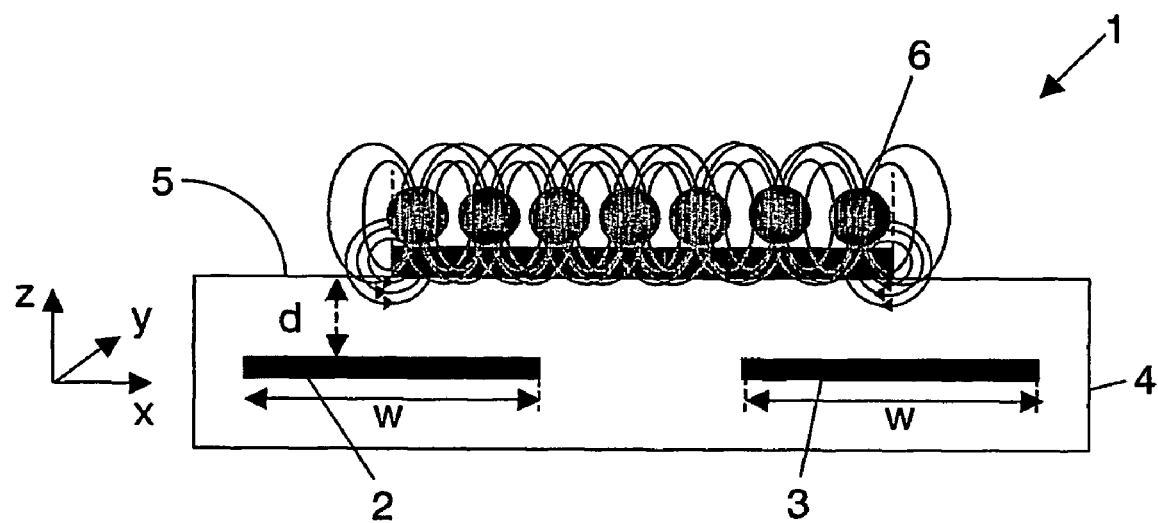
FIG. 1 is a cross-section of part of a biosensor, comprising GMR sensors, according to the prior art.

In the different figures, the same reference figures refer to the same or analogous elements.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The present invention provides an integrated circuit 10 and a method for noise removal during detection of nano-particles by means of a sensor device. The integrated circuit 10 may comprise at least one magnetic field generator 11, at least one magneto-resistive sensor 12 and at least one noise optimisation circuit 13. The magnetic field generator 11 may for example be a current wire. The magneto-resistive sensor 12 may for example be a GMR, a TMR or an AMR type sensor and may for example have an elongate geometry, e.g. a long and narrow stripe geometry, but the invention is not limited to this geometry. The magnetic field generator 11 may be positioned close to the magneto-resistive sensor 12 such that the magnetic field generator 11 generates a magnetic field in such a way that the magnetic field strength inside the magneto-resistive sensor 12 is stabilised in a region where the SNR is maximal. Prior to bio-measurements, an optimal operation point of the device is determined by optimising the SNR at the output of the sensor 12.

Because the course of the noise as a function of the magnetic field strength may be whimsical, which means that there is no gradient available, an iterative process may search for the optimal region within the borders of the detection curve. The method described above will further be explained by means of different embodiments described hereinafter.

Figure 2:
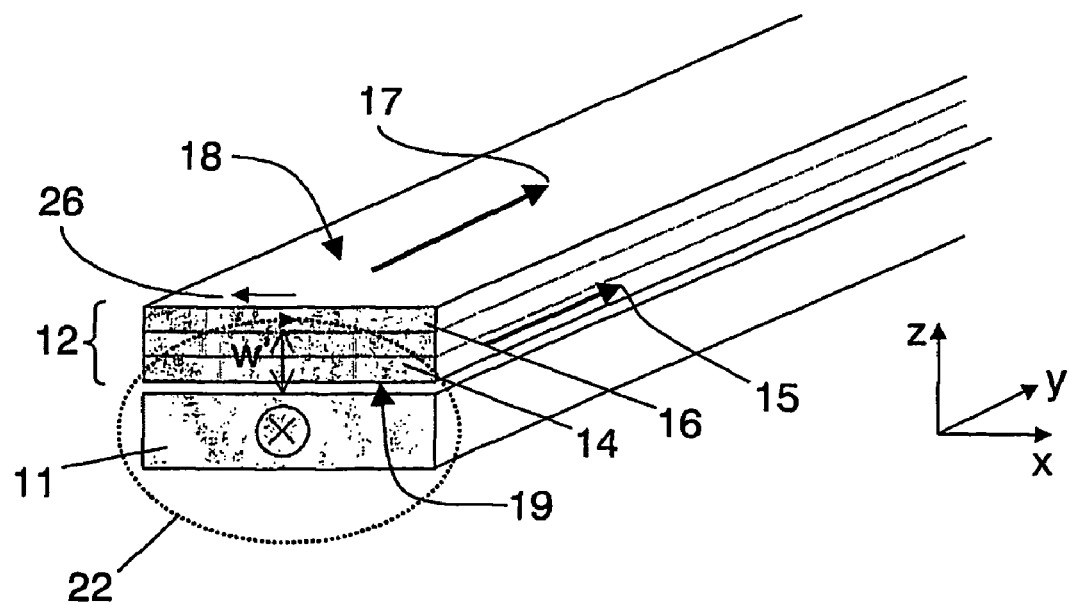
FIG. 2 shows a device according to a first embodiment of the present invention.
Figure 3:
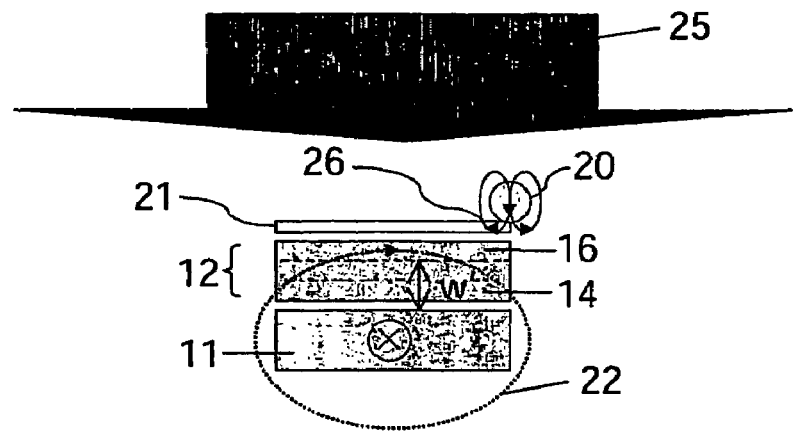
FIG. 3 is a cross-sectional view of the device of FIG. 2.
Figure 4:
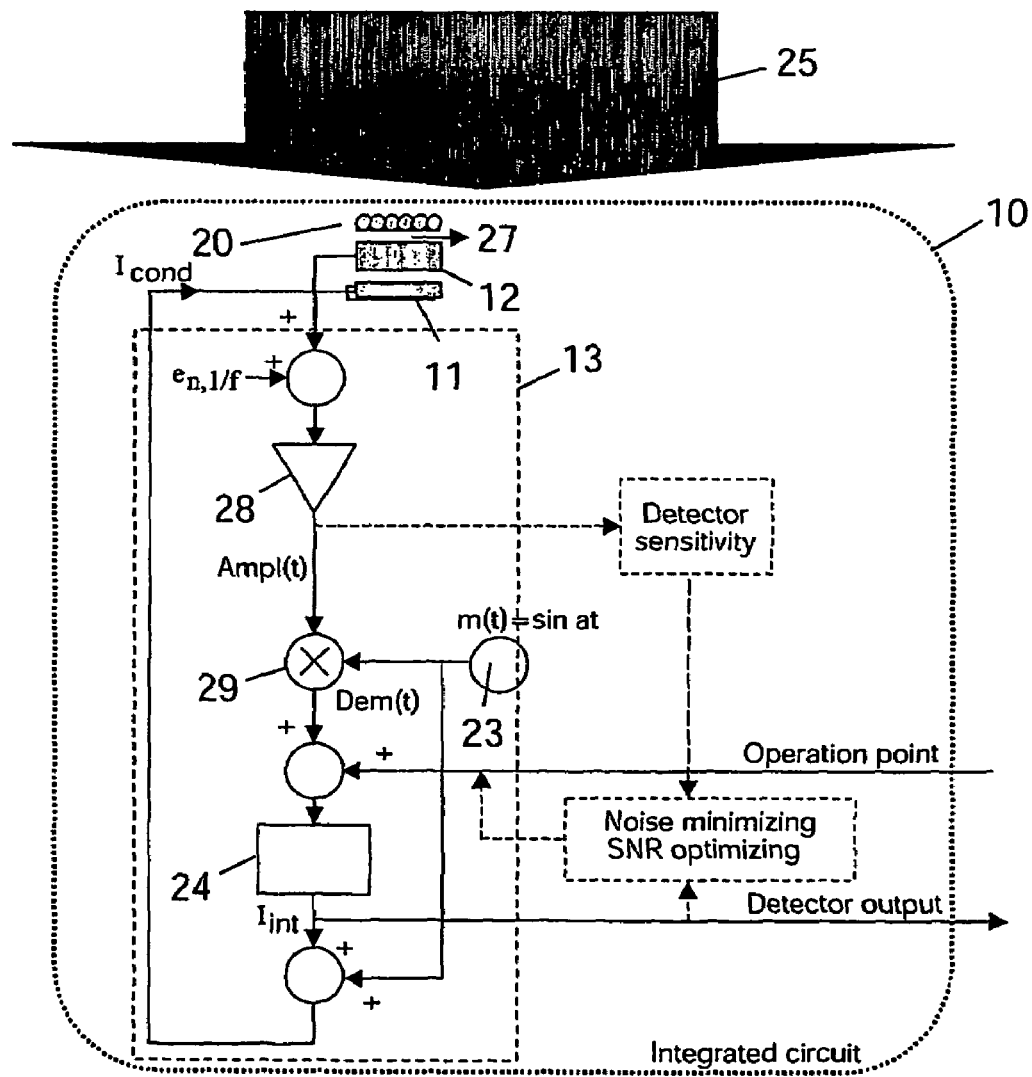
FIG. 4 is a schematic view of an integrated circuit illustrating a method of the present invention according to the first embodiment.

A first embodiment of the present invention is illustrated in FIG. 2 to FIG. 4. The integrated circuit 10 may comprise a magneto-resistive sensor 12, which may for example be a GMR element having an even, i.e. symmetrical, R(H) characteristic. Such an even R(H) characteristic may be achieved by magnetising the pinned layer 14 of the GMR sensor 12 along the easy axis or y-axis of the geometry, as shown in FIG. 2. The magnetisation direction in the pinned layer 14 is indicated by arrow 15. The preferred magnetisation in the free layer 16 of the magneto-resistive sensor 12, according to the easy axis, is indicated by arrow 17. The GMR sensor 12 may furthermore comprise an upper 18 and a lower 19 side, the upper 18 and lower 19 side being opposite to each other.

Furthermore, the device may comprise a conductor 11 as a magnetic field generator, which is positioned at the lower side 19 of the magneto-resistive sensor 12. At the upper side 18 of the GMR sensor 12 a surface is positioned at which nano-particles 20 may be immobilised as a result of a biological assay. This surface is called immobilise-surface 21. This means that for measuring the particle bulk concentration, no surface modification is required. Only if the concentration of bonded nano-particles 20 immobilised on the surface must be measured, surface modification is required. When immobilised nano-particles 20 must be detected, the chip comprises a top-layer 21 or immobilising-surface 21 as described above, which is mostly gold but may be any other suitable material, for deposition of the biomaterials.

Prior to a biochemical measurement, i.e. before magnetic nano-particles 20 are present in the neighbourhood of the magneto-resistive sensor 12, the optimal operation point of the sensor 12 is determined by minimizing the noise at the output of the sensor 12 and calibrating this output to be zero. An iterative process may be required to search for the optimal working region of the sensor 12. For the optimal operation point, the signal to noise ratio needs to be as high as possible and is preferably 1 or higher. The absolute value of the SNR depends on the amplitude of an applied external magnetic field 25 and on the sensor noise power.

In FIG. 4 a schematic view of an integrated circuit according to the first embodiment of the present invention is shown. By driving a current through the conductor 11, the conductor 11 generates a magnetic field which stabilises the magnetic field strength in the sensor 12, hereby generating a first horizontal field component 22 at the location of the sensor 12. As can be seen from FIG. 4, the conductor current $I_{cond}$ is the sum of a modulating signal, m(t)=sin at, generated by a harmonic modulation source 23 and the output $I_{int}$ of an integrator 24. Hence:

$$I_{cond}=I_{int}+\sin at \quad (Eq.1)$$

In order to achieve high reduction, the integrator 24 may preferably be a first- or higher order integrating loop filter.

Magnetic nano-particles 20 are then brought in the vicinity of the magneto-resistive sensor 12 and an external magnetic field 25 (FIG. 3), which may be generated by for example a permanent magnet, is applied to the magnetic nano-particles 20 which are immobilised at the immobilise-surface 21, hereby magnetising the immobilised nano-particles 20 in a direction imposed by the external magnetic field 25, which is a vertical direction in the example shown in FIG. 3. More generally, the external magnetic field 25 may be applied in a direction perpendicular to the sensitive direction of the magneto-resistive sensor 12. However, in practice, the external field 25 is often not perfectly perpendicular. The invention can thus also be used to compensate the effect of a non-perpendicular magnetic field. Therefore, it is included within the scope of the present invention to position the external magnetic field generator at an angle with respect to a perpendicular to the sensor device. However, this can easily saturate the sensor 12 because the external magnetic field 25 is much larger than the dynamic range of the sensor 12. The invention can also prevent saturation of the GMR sensor. As a result of the applied external field 25 a second horizontal field component 26 arises in the GMR sensor 12. After starting the biochemical measurement, the change in the magnetic field strength due to the nano-particles 20 is measurable at the output of the integrator 24. Both $I_{int}$ and m(t) now generate horizontal field components at the location of the GMR sensor 12, i.e.

resp. first 22 and second 26 horizontal field components. The net magnetic field 27 at the GMR sensor 12 is proportional or equal to the contribution of the conductor current and the field from the nano-particles 20, hence:

$$H_{GMR} \propto I_{cond} + H_{ext} N_{nano} = (I_{int} + \sin at) + H_{ext} N_{nano} = A + \sin at \quad (Eq.2)$$

wherein $H_{GMR}$=the net magnetic field at the GMR sensor
$H_{ext}$=the external magnetic field 25
$N_{nano}$=the number of magnetic nano-particles present in the system and where the average magnetic field A inside the sensitive layer of the sensor 12 equals:

$$A = I_{int} + H_{ext} N_{nano} \quad (Eq.3)$$

Due to the even R(H) characteristic:

$$R(H) \propto H^2 = (A + \sin at)^2 \quad (Eq.4)$$

The building block with note $e_{n,1/f}$ in FIG. 4 is nothing more than a schematic representation of the fact that the signal coming from the magneto-resistive sensor 12 comprises 1/f noise. This building block has no further function in the integrated circuit and will therefore not be mentioned furthermore in the description of this invention.

The signal measured by the magneto-resistive sensor 12 is then delivered to an amplifier 28 for amplification, thus generating an amplified signal Ampl(t). The amplified signal Ampl(t) is synchronously demodulated by passing through a demodulating multiplier 29 with the modulation signal m(t), resulting in an intermediate signal dem(t), the intermediate signal dem(t) being equal to:

$$dem(t) = (A + \sin at)^2 \cdot \sin at = A^2 \sin at + 2A \sin^2 at + \sin^3 at$$

$$dem(t) = (A^2 + \sin^2 at)\sin at + A - A\cos 2at \quad (Eq.5)$$

It is assumed that for the optimal operation point, A equals to zero. After integration by the integrator 24, the conductor current $I_{cond}$ is adjusted so that the magnetic field originating from the immobilised nano-particles 20, i.e. the second horizontal magnetic field component 26, is compensated and hence:

$$A = I_{int} + H_{ext} N_{nano} = 0 \quad (Eq.6)$$

The magnitude of the current $I_{int}$ required to compensate for the second horizontal field component 26 is therefore dependent on the number of nano-particles 20 immobilised on the immobilise-surface 21.

By adding an offset value to the input of the integrator 24, the field strength in the GMR sensor 12 is stabilised at an operation point different from zero. By varying the current in the magnetic field generator via the 'operation point' input, e.g. by means of a current control means, the magnetic field in the sensor 12 is varied. By measuring the noise power (e.g. at the integrator output) and the amplitude of the response of the harmonic modulation source 23 m(t)=sin(at), which depends on the local slope of the R(H) characteristic, at the output of the GMR amplifier 28 the signal-to-noise ratio can be measured and optimised. Noise power measuring means and amplitude determining means may be provided for outputting a value representative of the noise power and/or amplitude of the response. Further control means may be provided for selecting an operation point leading to the maximal SNR in a sufficient wide region as the operation point of the detector. Such means may comprise a noise minimizing algorithm. The noise minimizing algorithm may be integrated on the chip or may be located outside the chip, such as for example in a reader station.

The achievable magnetic field strength for the proposed embodiment may be derived as follows. Assuming that the magneto-resistive sensor 12 has a long and narrow stripe geometry, that the distance w between the conductor 11 and the sensitive layer in the GMR sensor 12 is 0.5 um and that the conductor current $I_{cond}$=20 mA, the vertical field strength equals to:

$$H_z = \frac{I_{cond}}{2\pi w} = \frac{0.02}{2\pi \cdot 0.5 \cdot 10^{-6}} \approx 6 kA/m \quad (Eq.7)$$

The operation point of the sensor 12 may be stabilised within a range of +/−6 kA/m. This means that the conductor 11 is able to generate a field from −6 to +6 kA/m using a current of −20 mA to 20 mA.

The magnetic field deviation caused by the magnetic nano-particles 20, which may typically be 0.4 A/m for 50 nm nano-particles 20 at 1 nano-particle/$\mu m^2$ surface density, is much smaller than this range.

Figure 5:
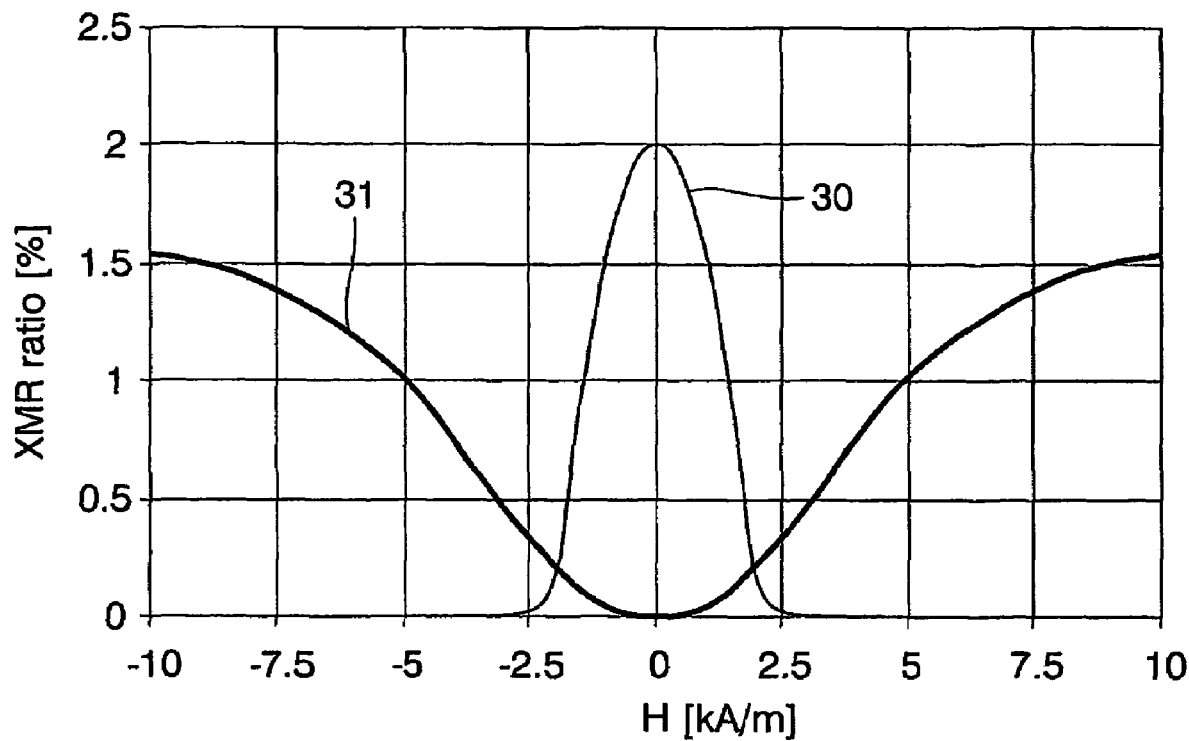
FIG. 5 shows an even R(H) characteristic for an AMR and GMR sensor.

FIG. 5 shows the transfer functions for 3 $\mu m$ wide AMR stripe sensors 12 (graph 30) and GMR stripe sensors 12 (graph 31) according to the above proposed device geometry. AMR sensors show steeper transfer functions 30 which give a better error signal than the transfer function of the GMR sensor 31. Therefore, AMR sensors may be more appropriate for application in the integrated circuit and method for noise removal of this first embodiment of the present invention.

In this embodiment, only the minimizing of the noise removal is discussed. For optimal SNR, also the sensitivity of the detection curve must be taken into account. This may be derived via an additional wobbling technique or from the present wobble amplitude, which is known for a person skilled in the art. The amplitude of the response of the wobble at the output of the amplifier 28 is a measure for the local sensitivity of the GMR element 12. A value representative of the amplitude can be obtained by rectifying, by an FFT or by synchronous demodulation.

In a further embodiment, the magnetic field generator 11 may be integrated in the magnetoresistive sensor 12, thus forming an integrated sensor 12/magnetic field generator 11 device. This integrated sensor/magnetic field generator 11 device both generates and detects the magnetic field. However, the allowable sensor current is now smaller than the conductor current $I_{cond}$ allowed in the first embodiment due to power dissipation in the high ohmic sensor 12/magnetic field generator 11 device. By varying the sensor current, the magnetic field inside the GMR sensor 12 may be changed in order to optimise the SNR.

A disadvantage of the first embodiment is the fact that common mode magnetic fields, i.e. average magnetic field A, are not suppressed. An external magnetic field 25 from for example magnets, transformers etc. is detected too. By implementing a bridge (differential) configuration (see further embodiments) the common-mode or overall field components are attenuated.

Figure 6:
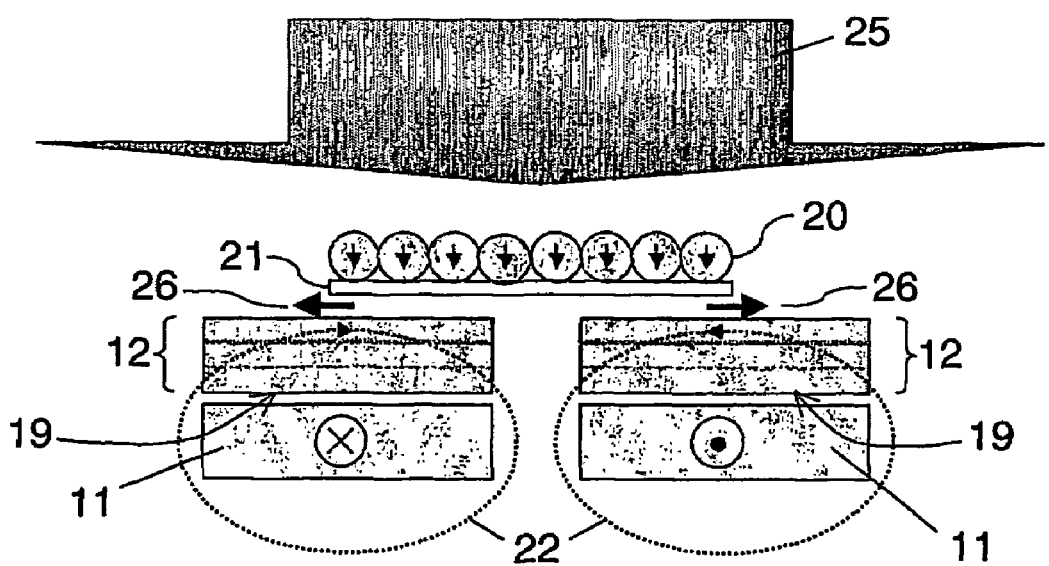
FIG. 6 is a cross-sectional view of a device according to a second embodiment of the present invention.
Figure 7:
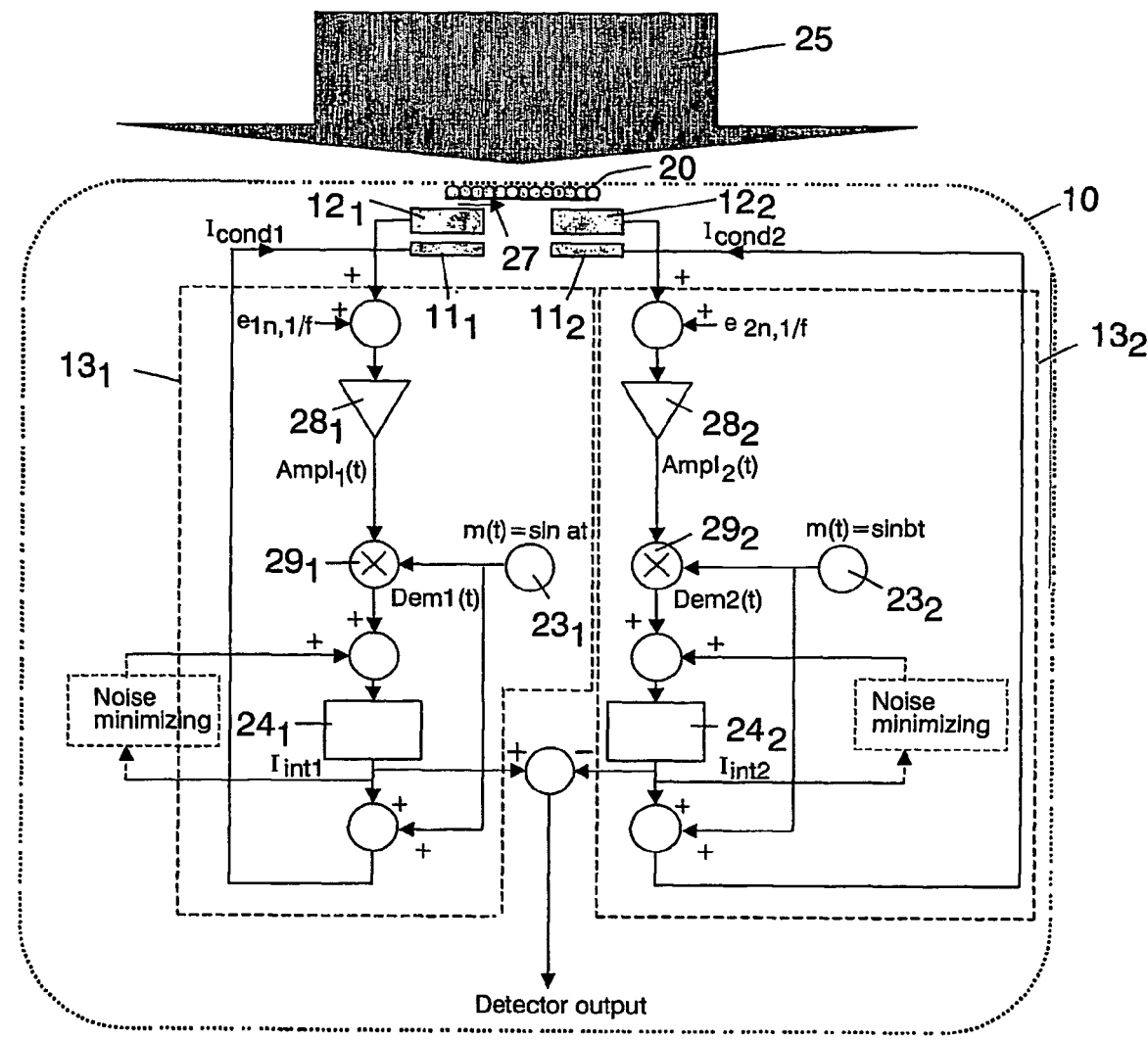
FIG. 7 is a schematic view of a method of the present invention according to the second embodiment of the present invention

A way to solve this problem is described in an improved embodiment, which is illustrated schematically in FIG. 6 and FIG. 7. The integrated circuit 10 of this improved embodiment may comprise two magneto-resistive sensors 12$_1$, 12$_2$ which are used in a balanced configuration, also called a differential measurement as described in the paragraph above.

The integrated circuit 10 may furthermore comprise 2 magnetic field generators, such as conductors 11$_1$, 11$_2$. Each conductor $11_1$, $11_2$ may be positioned at the lower side 19 of a magneto-resistive sensor $12_1$, $12_2$ (FIG. 6).

Each sensor $12_1$, $12_2$ comprises a noise optimisation circuit $13_1$, $13_2$ in order to minimise the noise at the output of the integrator $24_1$, $24_2$ (FIG. 7). The noise minimizing algorithm may be integrated on the chip or may be located outside the chip, such as for example in a reader station.

Prior to a biochemical measurement the optimal operation point of each of the sensors $12_1$, $12_2$ is determined by minimizing the noise or optimising the SNR at the output of each sensor $12_1$, $12_2$, as described in the first embodiment. After optimisation, the difference between the two integrator values (the detector output signal), may be calibrated to zero.

Then, the nano-particles 20 may be brought in the vicinity of the magneto-resistive sensors $12_1$, $12_2$ and the bio-measurement may start. Due to the balanced configuration, common mode magnetic fields are suppressed.

In FIGS. 6 and 7, the immobilise-surface 21 is shown as covering only half of each sensor 12. That is because, if an even R(H) characteristic is 'controlled' to a non-zero magnetic field the behaviour of the sensor 12 is like an odd R(H) characteristic and then, one half of the sensor 12 must be insensitive for nanoparticles 20 (see further). However, at zero field the nanoparticles 20 can be located over the total area of the chip. In that case, the sensitivity will decrease at large distance from the sensor 12.

In this embodiment the 'balanced behaviour' of the two sensors is maintained when the slope of the sensors are in the same direction. This slope depends on the position of the operation point on their characteristic.

When the two slopes are not in the same direction, the two integrator values must be added instead of subtracted, in order to achieve a balanced configuration. The direction of the slope can be determined by adding a harmonic modulation to the field generator currents and synchronous demodulate them (like the sensitivity measurement in embodiment 1), or from the lowpass filtered Dem1 and Dem2.

Figure 8:
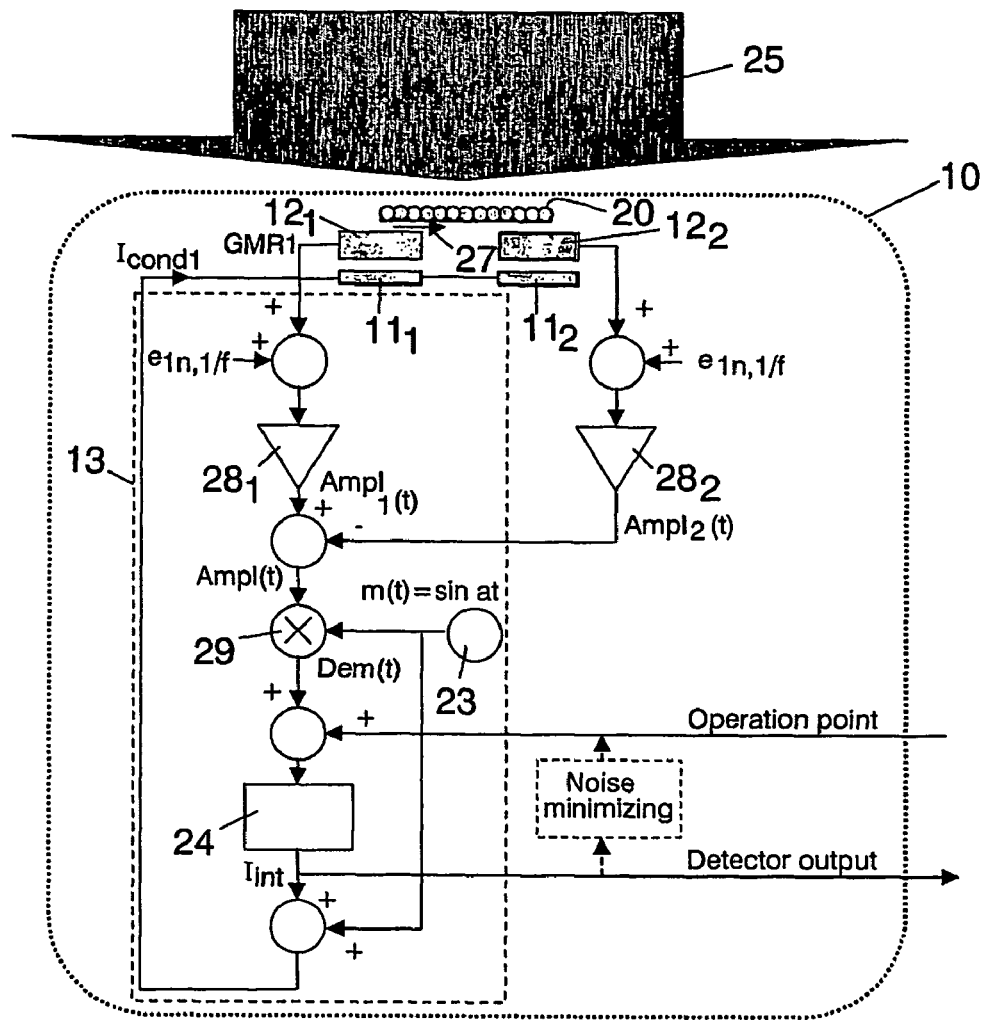
FIG. 8 is a schematic view of a method of the present invention according to a specific example of the second embodiment.

In a specific example of the second embodiment, the noise properties of both magneto-resistive sensors $12_1$, $12_2$ may be equal. In that case only one control loop or noise optimising circuit 13 is needed to stabilise the magnetic fields in both magneto-resistive sensors $12_1$, $12_2$. This is illustrated in FIG. 8.

The signals measured by resp. the first and second magneto-resistive sensor $12_1$, $12_2$ go to resp. a first and a second amplifier $28_1$, $28_2$ for amplification, thus generating the amplified signals $Ampl_1(t)$ and $Ampl_2(t)$. The amplified signal $Ampl_2(t)$ is then subtracted from the amplified signal $Ampl_1(t)$, resulting in the signal $Ampl(t)$. The signal $Ampl(t)$ is then synchronously demodulated by passing through a demodulating multiplier 29 with the modulation signal m(t), resulting in an intermediate signal dem(t). The optimal operation point of both magneto-resistive sensors $12_1$, $12_2$ is determined by minimizing the noise at the output of the sensors $12_1$, $12_2$.

Figure 9:
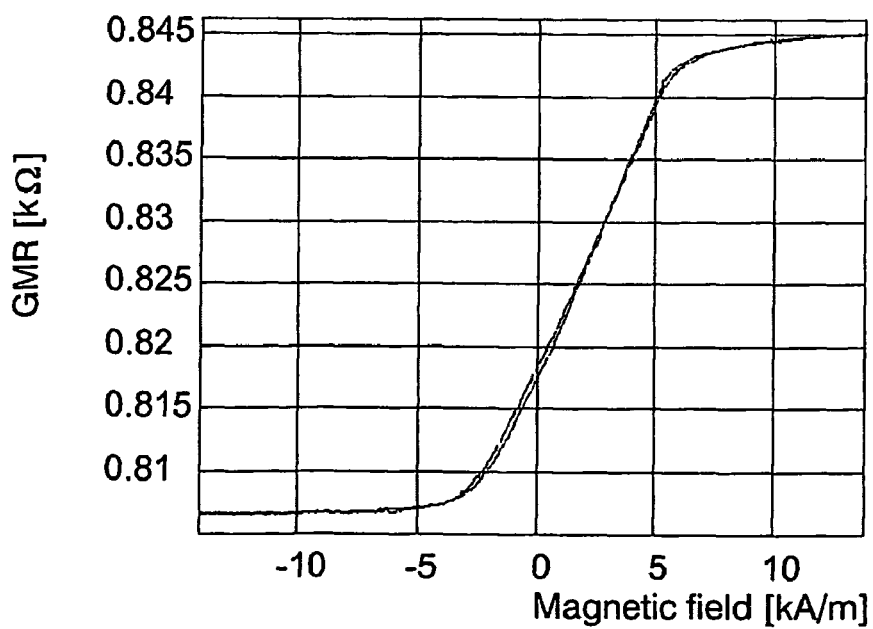
FIG. 9 shows an odd R(H) characteristic of a GMR strip sensor.
Figure 10:
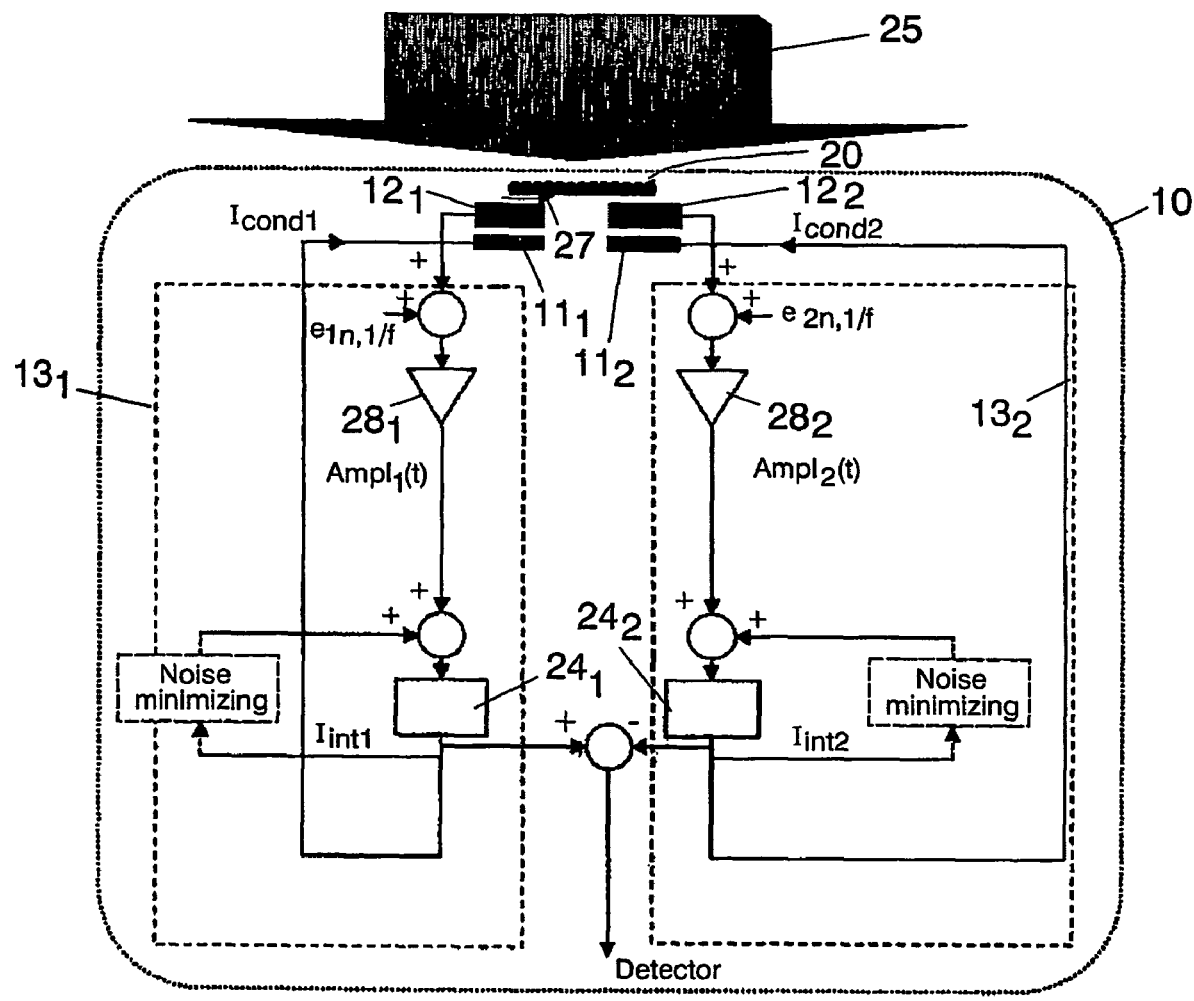
FIG. 10 is a schematic view of a method of the present invention according to a third embodiment

In another embodiment, which is illustrated in FIG. 10, the method and device of the present invention may be used to stabilise the operation point of a magneto-resistive sensors $12_1$, $12_2$ having an odd R(H) characteristic (FIG. 9). The integrated circuit 10 may comprise two magneto-resistive sensors $12_1$, $12_2$ and two magnetic field generators, such as conductors $11_1$, $11_2$. A conductor $11_1$, $11_2$ may be positioned at the lower side 19 of each sensor $12_1$, $12_2$. Furthermore, the integrated circuit 10 may comprise two noise optimisation circuits $13_1$, $13_2$. In this embodiment, due to the odd characteristic of the sensors $12_1$, $12_2$, the noise optimisation circuit $13_1$, $13_2$ does not require a harmonic modulation source 23. Hence, $I_{cond1}=I_{int1}$ and $I_{cond2}=I_{int2}$. A schematic view of the method according to this third embodiment of the present invention is shown in FIG. 10. The signal measured at the first and second sensors $12_1$, $12_2$, due to the net magnetic field 27, which is the summation of a first 22 and second 26 magnetic field component, is sent through a first and a second amplifiers $28_1$, $28_2$ for amplification, thus generating the signal $Ampl_1(t)$ resp. $Ampl_2(t)$. The signal may then be iteratively sent to the integrators $24_1$, $24_2$ in order to optimise the noise of the sensors $12_1$, $12_2$.

Prior to the bio measurement each sensor $12_1$, $12_2$ is optimised as described above without magnetic nano-particles 20 in the neighbourhood. After optimisation, the difference between the two integrator values (the detector output signal), may be calibrated to zero. When nano-particles 20 are present in the vicinity of the magneto-resistive sensors $12_1$, $12_2$, the concentration of the nano-particles 20 may be determined by adjusting the conductor current in order to compensate for the second horizontal magnetic field component 26 originating for magnetized nano-particles 20. The magnitude of the current required for this compensation is a measure for the amount of nano-particles 20 present at the upper side 18 of the sensors $12_1$, $12_2$.

In this embodiment, the sensor device needs some measures to limit the nano-particles 20 to one half of each sensor 12 (as depicted in FIG. 10), because otherwise the response to the nano-particles 12 cancels. This can be achieved by applying no gold (immobilise-surface 21) layer above one half of the sensors 12.

Figure 11:
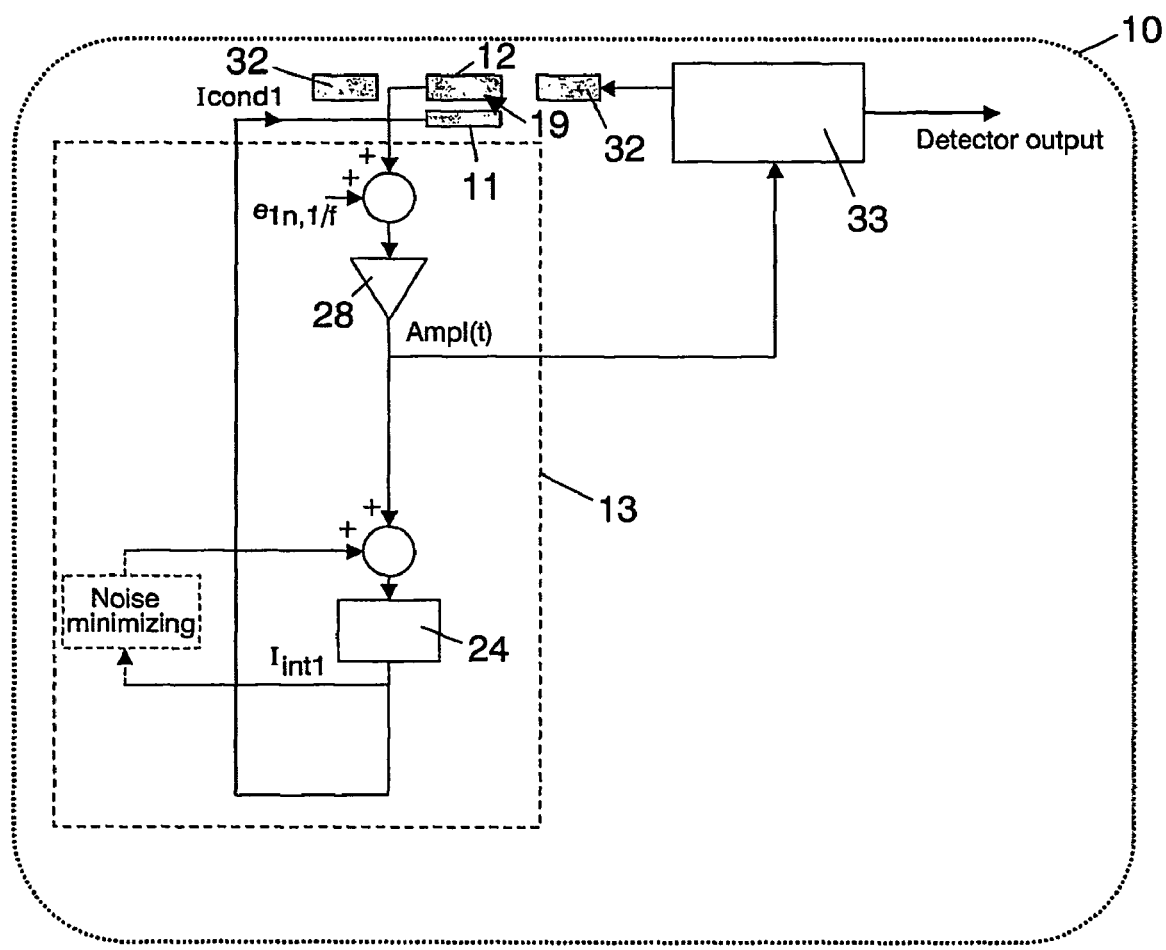
FIG. 11 is a schematic view of a method of the present invention according to a fourth embodiment.

In a fourth embodiment, the integrated circuit 10 and method for noise removal of the present invention may be applied in an on-chip magnetic particle sensor device, as depicted in FIG. 11.

In this embodiment, the integrated circuit may comprise a magneto-resistive sensor 12 and a magnetic field generator such as a conductor 11 that is positioned at the lower side 19 of the magneto-resistive sensor 12. Furthermore, the integrated circuit may comprise at least one additional magnetic field generator such as conductor 32 positioned adjacent the magneto-resistive sensor 12, this at least one additional conductor 32 serving as external magnetic field generator (FIG. 11).

The function of the magnetic field generator 11 can also be added to the functionality of the additional conductor 32 by aligning the additional conductor 32 and the sensor element 12 such that a magnetic field component appears in the sensitive direction of the sensor element 12.

Furthermore, the integrated circuit in FIG. 11 may comprise a detection means 33. Noise optimisation may be applied in the same way as described in the third embodiment of this invention.

The method of the present invention, described in the above embodiments, may also be applied during the manufacturing of an integrated circuit 10. By applying the method, the optimal operation point is determined and stored into the chip during the manufacturing process.

Furthermore, the integrated circuit, according to the present invention, may be used for molecular diagnostics, biological sample analysis or chemical sample analysis.

An advantage of the present invention is the fact that the sensor noise power does not change when an external magnetic field 25 is applied. Furthermore, the field generating elements 11, which are present on the chip, generate a magnetic field that depends on the amplitude of the applied external magnetic field 25.

It is to be understood that although preferred embodiments, specific constructions and configurations, as well as materials, have been discussed herein for devices according to the present invention, various changes or modifications in form and detail may be made without departing from the scope and spirit of this invention.

The invention claimed is:

1. An integrated circuit (10) for noise removal in a magnetic nano-particle sensor device, the integrated circuit comprising:
at least one first magnetic field generator (11) and at least one magneto-resistive sensor (12), said at least one first magnetic field generator (11) being suitable for generating a first magnetic field component (22) in a sensitive direction of the at least one magneto-resistive sensor (12),
means for determining an operation point of the at least one magneto-resistive sensor (12),
there being a second magnetic field generator for generating a magnetic field for magnetising the nano-particles (20) to thereby generate a second magnetic field component (26) in the sensitive direction of the at least one magneto-resistive sensor (12)
the integrated circuit furthermore comprising at least one noise optimisation circuit (13) adapted for stabilising the net magnetic field strength in the sensor (12) by compensating for said second magnetic field component (26).

2. An integrated circuit (10) according to claim 1, wherein said second magnetic field generator is a magnetic field generator external to the integrated circuit (10).

3. An integrated circuit (10) according to claim 1, wherein, for said operation point, the signal to noise ratio is at least 1.

4. An integrated circuit (10) according to claim 1, wherein said at least one first magnetic field generator comprises a conductor (11).

5. An integrated circuit (10) according to claim 1, wherein said at least one magneto-resitive sensor (12) comprises an upper side (18) and a lower side (19), said upper side (18) and lower side (19) being opposite to each other, and wherein the at least one magnetic field generator (11) is positioned at the lower side (19) of the at least one magneto-resistive sensor (12).

6. An integrated circuit (10) according to claim 5, the integrated circuit (10) comprising two magneto-resistive sensors ($12_1$, $12_2$) adjacent to each other and a magnetic field generator ($11_1$, $11_2$) positioned at the lower side (19) of each magneto-resistive sensor ($12_1$, $12_2$).

7. An integrated circuit (10) according to claim 1, wherein said magneto-resistive sensor (12) has a long and narrow stripe geometry.

8. An integrated circuit (10) according to claim 1, wherein said first magnetic field generator (11) is integrated into said magnetoresistive sensor (12).

9. An integrated circuit (10) according to claim 1, wherein said noise optimisation circuit (13) comprises an integrator device (24).

10. An integrated circuit (10) according to claim 1, wherein said noise optimisation circuit (13) furthermore comprises a harmonic modulation source (23).

11. An integrated circuit (10) according to claim 1, wherein the second magnetic field generator comprises one or more conductors (32).

12. A biochip comprising the integrated circuit according to claim 1.

13. A method for noise removal in a magnetic nano-particle sensor device, the method comprising:
generating a first magnetic field component (22) in a sensitive direction of a magneto-resistive sensor (12),
determining an operation point of the magneto-resistive sensor (12) by minimizing the noise at the output of said magneto resistive sensor (12)
applying a second magnetic field (25) for magnetising nano-particles (20), thus generating a second magnetic field component (26) in the sensitive direction of the magneto-resistive sensor (12)
adjusting the first magnetic field component (22) 50 as to compensate for said second magnetic field component (26).

14. A method according to claim 13, wherein determining an operation point of the magneto-resistive sensor (12) comprises determining an operation point for which the signal to noise ratio is at least 1.

15. A method according to claim 13, wherein generating a first magnetic field component comprises flowing a conductor current through a conductor (11).

16. A method according to claim 15, wherein adjusting the first magnetic field component is performed by adjusting the conductor current through the conductor (11).

17. A method according to claim 13, the method furthermore comprising:
determining an operation point of a second magneto-resistive sensor ($12_2$) by minimizing the noise at the output of said second magneto-resistive sensor ($12_2$),
calibrating the difference between the output of said first magneto-resistive sensor ($12_1$) and said second magneto-resistive sensor ($12_2$) to zero.

18. A method according to claim 17, wherein determining an operation point of the second magneto-resistive sensor ($12_2$) comprises determining an operation point for which the signal to noise ratio is at least 1.

19. A method according to claim 13, wherein said second magnetic field (25) is generated by one or more additional conductors (32).

20. A method according to claim 13, wherein the method is applied during the manufacturing of an integrated circuit (10).

21. Use of the integrated circuit as claimed in claim 1 for molecular diagnostics, biological sample analysis or chemical sample analysis.

* * * * *